United States Patent [19]

Milhaud

[11] Patent Number: 5,656,723
[45] Date of Patent: Aug. 12, 1997

[54] ANALOGUES OF HYPOCALCEMIANT POLYPEPTIDE COMPOUNDS SPARING THE CALCIUM OF THE ORGANISM, THEIR PREPARATION, THEIR USE AS MEDICAMENTS AND THE COMPOSITIONS CONTAINING THEM

[76] Inventor: Gérard Milhaud, 7, rue des Saints Pères, Paris, France, 75006

[21] Appl. No.: 397,713

[22] Filed: Mar. 2, 1995

Related U.S. Application Data

[63] Continuation of Ser. No. 232,586, Apr. 25, 1994, abandoned, which is a continuation of Ser. No. 47,390, Apr. 8, 1993, abandoned, which is a continuation of Ser. No. 912,588, Jul. 13, 1992, abandoned, which is a continuation of Ser. No. 789,043, Nov. 7, 1991, abandoned, which is a continuation of Ser. No. 650,990, Feb. 4, 1991, abandoned, which is a continuation of Ser. No. 97,520, filed as PCT/FR86/00440, Dec. 11, 1986, abandoned.

[30] Foreign Application Priority Data

Dec. 24, 1985 [FR] France .................. 85 19113

[51] Int. Cl.⁶ .................. A61K 38/00; C07K 5/00; C07K 7/00; C07K 17/00
[52] U.S. Cl. .................. 530/307; 530/317; 530/324; 530/333; 530/334; 530/338
[58] Field of Search .................. 530/307, 324, 530/333, 334, 338, 317; 514/11, 12, 808

[56] References Cited

U.S. PATENT DOCUMENTS

| | | |
|---|---|---|
| 3,926,938 | 12/1975 | Hughes et al. . |
| 4,217,268 | 8/1980 | Hughes et al. .................. 530/307 |
| 4,528,132 | 7/1985 | Orlowski et al. .................. 530/307 |
| 4,537,716 | 8/1985 | Orlowski et al. .................. 530/307 |
| 4,622,388 | 11/1986 | Orlowski et al. .................. 530/307 |
| 4,703,106 | 10/1987 | Hirose et al. .................. 530/307 |
| 4,737,487 | 4/1988 | Watts et al. .................. 514/15 |
| 4,764,591 | 8/1988 | Orlowski et al. .................. 530/307 |

FOREIGN PATENT DOCUMENTS

| | | |
|---|---|---|
| 2309235 | 11/1976 | France . |
| 2521553 | 8/1983 | France . |

OTHER PUBLICATIONS

Robson et al., Introduction to Proteins and Protein Engineering, Amsterdam, New York, Oxford (Published by Elsevier Science Publishers) pp. 323–325 (1986).
Lehringer, Biochemistry, Worth Publishers, Inc. pp. 95–117 (1982).
Potts et al., The Handbook of Physiology, Section 7, Endocrinology, vol. VII, Greep et al. (Ed.) American Physiological Society, Washington, D.C. pp. 423–430.
Milhaud, Actualites Pharmacologiques, pp. 8–9 (1978).
Guttmann, Calcitonin, A. Pecile (Ed.) pp. 11–23 (1980).
Azria, The Calcitonins, Karger, New York, pp. 17 and 19 (1989).
Dayhoff, Atlas of Protein Sequence and Structure vol. 5 pp. 89–99 1972.
A. Nieto, F. Moya and J.L. R–Candela, "Isolation and Properties of Two Calcitonins from Chicken Ultimobranchial Glands," *Biochimica et Biophysica Acta*, vol. 322, pp. 383–393 (1973).

*Primary Examiner*—Toni R. Scheiner
*Assistant Examiner*—Sheela J. Huff
*Attorney, Agent, or Firm*—Bacon & Thomas

[57] ABSTRACT

New polypeptides comprising 32 amino acids, process for preparation thereof, application thereof as drugs and pharmaceutical preparations containing, as active ingredient, one or a plurality of said polypeptides. These polypeptides are used as active principles for new drugs, particularly indicated for osteoporoses of various origins.

16 Claims, No Drawings

ANALOGUES OF HYPOCALCEMIANT POLYPEPTIDE COMPOUNDS SPARING THE CALCIUM OF THE ORGANISM, THEIR PREPARATION, THEIR USE AS MEDICAMENTS AND THE COMPOSITIONS CONTAINING THEM

This application is a File Wrapper Continuation of application Ser. No. 08/232,586, filed Apr. 25, 1994 (now abandoned); which is a File Wrapper Continuation of application Ser. No. 08/047,390, filed Apr. 8, 1993 (now abandoned); which is a File Wrapper Continuation of application Ser. No. 07/912,588, filed Jul. 13, 1992 (now abandoned); which is a File Wrapper Continuation of application Ser. No: 07/789,043, filed Nov. 7, 1991 (now abandoned); which is a Continuation of application Ser. No. 07/650,990, filed Feb. 4, 1991 (now abandoned); which is a Continuation of application Ser. No. 07/097,520, filed as PCT/FR86/00440, Dec. 11, 1986 (now abandoned).

The subject of the present invention is new polypeptide compounds, characterized in that they are chosen from the group formed by the products with the formula ($I_A$):

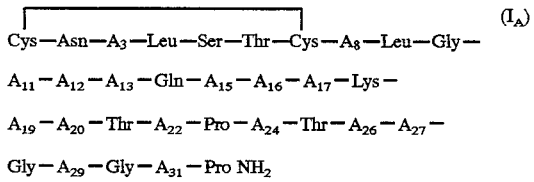

$$Cys—Asn—A_3—Leu—Ser—Thr—Cys—A_8—Leu—Gly—$$
$$A_{11}—A_{12}—A_{13}—Gln—A_{15}—A_{16}—A_{17}—Lys—$$
$$A_{19}—A_{20}—Thr—A_{22}—Pro—A_{24}—Thr—A_{26}—A_{27}—$$
$$Gly—A_{29}—Gly—A_{31}—Pro\ NH_2$$

where: $A_3$=Ser, Gly or Ala
$A_8$=Val or Leu
$A_{11}$=Lys or Thr
$A_{12}$=Leu or Tyr
$A_{13}$=Ser or Thr
$A_{15}$=Glu or Asp
$A_{16}$=Leu or Phe
$A_{17}$=His or Asn
$A_{19}$=Leu or Phe
$A_{20}$=Gln or His
$A_{22}$=Tyr or Phe
$A_{24}$=Arg or Gln
$A_{26}$=Asp, Asn or Ala
$A_{27}$=Val, Thr or Ile
$A_{29}$=Ala, Ser, or Val
$A_{31}$=Thr, Val or Ala and the products with the formula ($I_B$) which contain ∝-amino-suberic acid (Asu) of which the ω-carboxyl is fixed to the amino group of Asn:

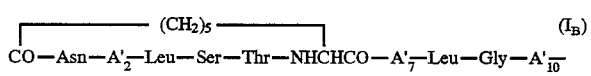

$$CO—Asn—A'_2—Leu—Ser—Thr—NHCHCO—A'_7—Leu—Gly—A'_{10}$$

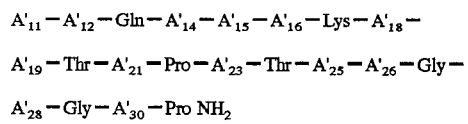

$$A'_{11}—A'_{12}—Gln—A'_{14}—A'_{15}—A'_{16}—Lys—A'_{18}—$$
$$A'_{19}—Thr—A'_{21}—Pro—A'_{23}—Thr—A'_{25}—A'_{26}—Gly—$$
$$A'_{28}—Gly—A'_{30}—Pro\ NH_2$$

where: $A'_2$=Ser, Gly or Ala
$A'_7$=Val or Leu
$A'_{10}$=Lys or Thr
$A'_{11}$=Leu or Tyr
$A'_{12}$=Ser or Thr
$A'_{14}$=Glu or Asp
$A'_{15}$=Leu or Phe
$A'_{16}$=His or Asn
$A'_{18}$=Leu or Phe
$A'_{19}$=Gln or His
$A'_{21}$=Tyr or Phe
$A'_{23}$=Arg or Gln
$A'_{25}$=Asp, Asn or Ala
$A'_{26}$=Val, Thr or Ile
$A'_{28}$=Ala, Ser or Val
$A'_{30}$=Thr, Val or Ala The products with the formula ($I_B$) are structural analogues of natural peptides, such as K. Jost and J. Rudinger realized in the case of neurohypophyseal hormones (Collect. Czech. Chem. Comm., 1967, 32, 1229).

The products with the formulae ($I_A$) and ($I_B$) can be regrouped into the following formula:

$$X—A'_7—Leu—Gly—A'_{10}—A'_{11}—A'_{12}—Gln—A'_{14}—A'_{15}— \quad (I)$$
$$A'_{16}—Lys—A'_{18}—A'_{19}—Thr—A'_{21}—Pro—A'_{23}—Thr—$$
$$A'_{25}—A'_{26}—Gly—A'_{28}—Gly—A'_{30}—ProNH_2$$

in which $A'_7, A'_{10}, A'_{11}, A'_{12}, A'_{14}, A'_{15}, A'_{16}, A'_{18}, A'_{19}, A'_{21}, A'_{23}, A'_{25}, A'_{26}, A'_{28}$ and $A'_{30}$ have the previous significance and X represents:
either the residue

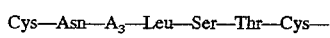

$$Cys—Asn—A_3—Leu—Ser—Thr—Cys—$$

in which $A_3$ has the previous significance
or the residue

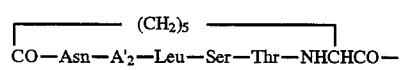

$$CO—Asn—A'_2—Leu—Ser—Thr—NHCHCO—$$

in which $A'_2$ has the previous significance.

The subject of the invention is in particular compounds answering to the general formulae ($I_A$) and ($I_B$), as defined previously, in which $A_8$ and $A'_7$ represent a valine.

The subject of the invention is more particularly compounds answering to the following general formulae ($I_A$) and ($I_B$):

—Cys—Asn—Ser—Leu—Ser₅—Thr—Cys—Val—Leu—

Gly₁₀—Lys—Leu—Ser—Gln—Glu₁₅—Leu—His—

Lys—Leu—Gln₂₀—Thr—Tyr—Pro—Arg—Thr₂₅—

Asp—Val—Gly—Ala—Gly₃₀—Thr-Proamide;

-continued

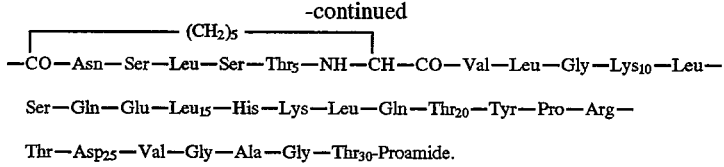

Ser—Gln—Glu—Leu$_{15}$—His—Lys—Leu—Gln—Thr$_{20}$—Tyr—Pro—Arg—

Thr—Asp$_{25}$—Val—Gly—Ala—Gly—Thr$_{30}$-Proamide.

The polypeptides according to the invention lower calcemia and phosphatemia; they inhibit bone destruction, accelerate formation of new bones, increase intestinal absorption of calcium and decrease calciurea. They fix calcium inside the cells. They possess an important anti-inflammatory and antalgic effect.

These properties justify the use of polypeptides with the formulae ($I_A$) and ($I_B$) as defined previously, as medicaments.

The subject of the invention is therefore also polypeptides with the formulae ($I_A$) and ($I_B$) as defined previously, as medicaments.

The subject of the invention is more particularly, as medicaments, the preferred polypeptides mentioned above.

The main indications of the medicaments according to the invention are represented by Paget's disease, osteoporoses of various etiologies (common, poro-malacic, cortisonic, post-traumatic, of immobilization and idiopathic), renal osteodystrophy, fractures, hypercalcemias, osteoarticular pains, in particular those resulting from bone metastases, spasmophilia and normocalcemic tetany.

The subject of the invention is also pharmaceutical compositions containing as active principle at least one of the medicaments as defined previously.

These pharmaceutical compositions can be, for example, solid or liquid and are presented in the pharmaceutical forms currently used in human medicine, like, for example, simple or sugar-coated tablets, capsules, granules, liposomes, aerosols, suppositories, injectable preparations; they are prepared according to the usual methods. The active principle or principles can be incorporated in the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various moistening, dispersing or emulsifying agents, and preservatives.

The subject of the invention is in particular pharmaceutical compositions as defined previously, characterized in that they are intended for parenteral administration, oral administration in the form of liposomes, or nasal administration in pulverized form.

The subject of the invention is also a preparation process for compounds as defined previously, characterized in that amino acids, peptides or their combinations, are submitted to condensation reactions in the order of the sequence of amino acids with the formulae ($I_A$) and ($I_B$), and by the fact that when the products with the formula ($I_B$) are prepared, the solid phase technique for obtaining the 10–31 sequence and the classic liquid phase technique for obtaining the 1–9 sequence are combined.

As previously indicated, the synthesis of peptides with the formula ($I_A$) and that of the 10–31 sequence of products with the formula ($I_B$) are carried out by using the solid phase technique. This brings into play benzylhydrylamino resin (P. G. Pietta and G. R. Marshall, Chem. Commun., 1970, 650), of which the preparation and use have been described (P. Rivaille, A. Robinson, M. Kamen and G. Milhaud, Helv., 1971, 54, 2772).

In a preferred way of preparation of products with the formula ($I_A$), the group N-α-butyloxycarbonyl (t-Boc) protects the α-amino function of the aminoacids. The lateral functions of the aminoacids are blocked in the form:

1) of benzyl ester for the carboxylic chain of aspartic and glutamic acids,
2) of benzyl ether for the hydroxyl of serine, threonine and of 2,4-dichlorobenzyl ether for tyrosine,
3) of methoxybenzyl ether for the sulphhydryl group of cysteine,
4) of dinitro-2,4-phenyl for the imidazol of histidine,
5) of the benzoxycarbonyl group for the ε-amino function of lysine.

The different amino acids are incorporated in the peptide chain by dicyclohexylcarbodiimide (DCCI) and hydroxybenzotriazol (HOBT) by making protected aminoacids in excess in relation to the proline first fixed on the resin react successively. The reaction is allowed to continue for two hours. The t-Boc groups are eliminated by trifluoroacetic acid in solution in methylene chloride; after washing with methylene chloride, neutralisation is carried out by triethylamine or diisopropylethylamine (DIEA) in the same solvent.

Asparagine and glutamine are introduced in the form of their para-nitrophenyl esters, in solution in dimethylformamide (DMF). If the control test for coupling to ninhydrin according to the method of Kaiser and Colescott is positive, the mixture is treated by pivalic acid (1%); if the blue colouration still persists in this test, the DMF/1% AcOH mixture is saturated with urea. However, even if this test is negative (no blue colouration), each coupling can be repeated twice systematically. If the coupling is not total at the end of 48 hours of reaction, as is the case for glutamine in position 20, the threonine which has not reacted is acetylated by acetyl-imidazol in methylene chloride or by acetic acid and DCCI.

Finally, the protector group of the imidazol of histidine is eliminated, while the peptide is still linked to the resin, at pH 8, with mercapto-ethanol in solution in DMF. The peptide is separated from the resin by treatment with liquid hydrofluoric acid in the presence of anisole and methionine. All the protector groups are eliminated during this operation.

The peptides are purified by filtration on gel. The fractions corresponding to the main peaks are assembled, lyophilized, taken up again in a buffer at pH 8 and oxidized for 24 hours by an air current in order to form the disulphide bridge between the two cysteine residues.

The fraction corresponding to the peak possessing the desired biological activity is again purified on ion exchange resin CMC 32 by an elution acid gradient. The peptide obtained is homogeneous to electrophoresis on paper and chromatography on cellulose.

The 10–31 sequence of products with the formula ($I_B$) is realized in the same conditions as those indicated previously for the preparation of products with the formula ($I_A$). What was indicated for glutamine in position 20 for products with the formula ($I_A$) is of course valid for position 19 for products with the formula ($I_B$).

In a preferred way of carrying out the preparation process for products with the formula $(I_B)$, the synthesis of the 1–9 sequence is carried out in a liquid medium. The fragment

where $A_2$ has the above significance and R=ester, is condensed after cyclization with the tripeptide $A_7$-Leu-Gly. Generally accepted protecting groups may be used in the synthesis of peptides.

The peptide of formula $(I_B)$ is then obtained as follows:

The above protected nonapeptide is converted into N-hydroxy-succinimide ester, then coupled with the 10–31 fragment fixed on the resin in DMF medium at 30° C. The peptide is separated from the resin by treatment with liquid hydrofluoric acid in the presence of dimethylsulphide and p-cresol (J. P. Tam, W. H. Heathand and R. B. Merrifield, J.A.C.S., 1983, 105, 6442). All of the protector groups are eliminated during this operation.

The peptides are purified by filtration on gel. The fractions corresponding to the principal peaks are reassembled and lyophilized. The fraction according to the peak possessing the desired biological activity is again purified on ion exchange resin CMC 32 by elution with the aid of a conductivity gradient. The peptide obtained after lyophilization appears to be homogeneous to electrophoresis on paper and chromatography on cellulose.

The following examples illustrate the invention without, however, limiting it.

EXAMPLE 1:

Obtaining peptide with the following formula $(I_A)$:

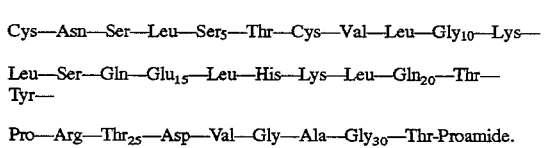

The t-Boc amino acids carrying the lateral functions come from BACHEM (Dubendorf, Switzerland) or are prepared in the laboratory by Schnabel's technique (E. Schnabel, Liebigs Ann. Chem., 702, 188, 1967) in an autotitration apparatus. Their purity is determined by polarimetry, melting point and chromatography on thin layer silica.

The hydrolysis of the purified peptide is carried out in a sealed tube under vacuum in a 6N HCl medium (110° C., 24 hours).

I. SYNTHESIS OF THE SEQUENCE a) Preparation of the resin (P. Rivaille, A. Robinson, M. Kamen and G. Milhaud, Helv., 1971, 54, 2772).

Benzyl-ketoresin

In a 2 l. three-necked flask, fitted with an agitator, 50 g of polystyrene with 1% of divinylbenzene Bio-rad $SX_1$ (200–400) is left to swell for 2 hours, in 350 ml of nitrobenzene. In another flask, 66 g of $AlCl_3$ is dissolved in 300 ml of nitrobenzene to which 80 ml of benzoyl chloride is added. The mixture is poured into the first flask under a good agitation which is maintained for 2 hours at ambient temperature. If the resin swells too much, nitrobenzene is added (about 100 ml). The mixture is filtered, washed with dioxan (3x), with acetic acid (3x), with methanol (3x) and finally, alternately, with $CH_2Cl_2$ and $CH_3OH$ in order to make the resin swell and contract each time leaving a sufficient contact time. The mixture is dried in a dessicator under vacuum all night (yield 75 g).

Benzylhydrylamine resin

In a 1 l. flask fitted with "Dean Stark" and an agitator, 500 g of ammonium formiate is heated to 120°–130° C., for 1 to 2 hours. The resin (50 g) is added in one go and the temperature is allowed to rise to 160°–165° C., over half an hour, under efficient agitation which is maintained for 6 hours. The mixture is washed with water, then treated as above for the benzylketoresin. The resin dried under vacuum is heated to reflux and agitated for 8 hours in 6N HCl. It is then filtered and washed as previously. The fixation capacity varies, according to the nature of the amino acid, between 0.3 and 0.5 mMole/g.

b) Preparation of the peptide

The apparatus used enables mechanical agitation of a 25 ml pyrex tube the central compartment of which contains the resin (2 g). At the ends of the tube, fritted glass filters are intended for the introduction and then the elimination of the reagents (about 15 ml).

The coupling of the amino acids involves the following times:

CYCLE 32

Coupling:

2 g of resin (fixation capacity 0.5 mMoles/g) is agitated (10 min) in a $CH_2Cl_2$, $(CH_3)_2NCHO$ (DMF) medium (1:1, v/v) in the presence of Boc-L-proline (2mM, 0.43 g). DCCI (4 mMoles) and 1-hydroxybenzotriazol (HOBT) (4 mMoles) are added and agitation is resumed for 2 hours. The resin is washed successively with $CH_2Cl_2$ (1x, 2 min), $CH_3OH$ abs (3x, 2 min), and $CH_2Cl_2$ (3x, 2 min). The reaction to ninhydrin is carried out on a sample of resin: it is negative.

Liberation of amino group:

The resin is treated by a $CF_3COOH$—$CH_2Cl_2$ mixture (1:1, v/v) for 1 min; the mixture is filtered and the operation is repeated leaving in contact for 15 min. The resin is washed with $CH_2Cl_2$ (3x, 1 min). $CF_3COOH$ is eliminated by treating the resin twice with an $Et_3N/CH_2Cl_2$ mixture (12.5: 87.5 v/v) (contact time 1 min then 5 min). It is washed with $CH_2Cl_2$ (8x, 1 min). The L-proline resin is titrated: it contains 0.5 mMole/g of proline.

CYCLE 31

Coupling:

The L-prolyl resin (1 mMole) is agitated (10 min) with 4 mMoles of Boc-O-Benzyl-L-threonine (1.23 g) in $CH_2Cl_2$-DMF (1:1 v/v) (10 ml). DCCI (4 mMoles) and HOBT (4 mMoles) are added and the agitation is resumed (2 hrs). The resin is washed successively: $CH_2Cl_2$ (1x, 2 min), $CH_3OH$ abs (3x, 2 min), $CH_2Cl_2$ (3x, 2 min). The reaction to ninhydrin is negative.

Liberation of the amine group—See cycle 32.

CYCLES 30 TO 25

The above coupling and liberation processes are used in making react for:

| | |
|---|---|
| Cycle 30 | 4 mMoles Boc-glycine (0.71 g) |
| Cycle 29 | 4 mMoles Boc-L-ala (0.76 g) |
| Cycle 28 | 4 mMoles Boc-glycine (0.71 g) |
| Cycle 27 | 4 mMoles Boc-L-valine (0.87 g) |
| Cycle 26 | 4 mMoles B-benzyl ester of Boc-L-aspartic acid (1.29 g) |
| Cycle 25 | 4 mMoles Boc-O-benzyl-L-threonine (1.24 g). |

CYCLE 24

Coupling:

The resin-peptide of cycle 25, previously washed with DMF (2x), is agitated (10 min) with 4 mMoles of Boc-N-γ-tosyl-L-arginine (1.41 g) in a solution of DMF and then the process is as described for cycle 31.

CYCLE 23

Coupling:

The peptide resin of cycle 24 is agitated (10 min) with 4 mMoles of Boc-L-proline (0.88 g in a $CH_2Cl_2$ medium) (10 ml). DCCI/HOBT is added as described for cycle 32. At the end of the reaction period, the reaction to ninhydrin is negative.

Liberation—See cycle 32.

CYCLES 22 TO 21

The coupling and liberation processes used in cycle 23 are used to make react:

| Cycle 22 | 4 mMoles Boc-O-Benzyl-L-tyrosine (1.49 g) |
| Cycle 21 | 4 mMoles Boc-O-Benzyl-L-threonine (1.24 g). |

CYCLE 20
Coupling:

The resin-peptide of cycle 21, previously washed with DMF (2x) is agitated (10 min) with 4 mMoles of Boc-L-glutamine p-nitrophenylester (1.5 g) and 10 ml DMF with the addition of 1% acetic acid. DCCI (4 mMoles) and HOBT (4 mMoles) are added and the mixture is agitated for 48 hours. The resin is washed with DMF, $CH_2Cl_2$, $CH_3OH$, $CH_2Cl_2$ (2x).

Liberation—See cycle 32.

CYCLES 19 TO 15

The process for cycle 31 is used to make react:

| Cycle 19 | 4 mMoles Boc-L-leucine (1.0 g) |
| Cycle 18 | 4 mMoles Boc-ε-carbobenzyloxy-L-lysine (1.52 g) |
| Cycle 17 | 4 mMoles Boc-dinitro-2,4-phenyl(im)L-histidine (1.23 g) |
| Cycle 16 | 4 mMoles Boc-L-leucine (1.0 g) |
| Cycle 15 | 4 mMoles γ-benzyl ester of Boc-L-glutamic acid (?) (1.3 g). |

CYCLE 14
The process is as for cycle 20.

CYCLE 13
The process is as for cycle 31, by using 4 mMoles of Boc-O-benzyl-L-serine (1.0 g).

CYCLES 12 TO 9

The process is as for cycle 31 making react:

| Cycle 12: | the derivative used in cycle 19. |
| Cycle 11: | the derivative used in cycle 18. |
| Cycle 10: | the derivative used in cycle 30. |
| Cycle  9: | the derivative used in cycle 19. |
| Cycle  8: | the derivative used in cycle 27. |

CYCLE 7

The process for cycle 31 is used making react 4 mMoles of S-p-methoxybenzyl ether of Boc-L-cysteine (1.13 g).

CYCLES 6 TO 3

| Cycle 6: | identical to cycle 31. |
| Cycle 5: | identical to cycle 13. |
| Cycle 4: | identical to cycle 19. |
| Cycle 3: | identical to cycle 13. |

CYCLE 2
Coupling:

The peptide resin from cycle 3 previously washed with DMF (2x) is agitated (48 hrs), with 4 mMoles of p-nitrophenyl ester of Boc-L-asparagine (1.45 g) in a DMF medium, in the presence of HOBT (4 mMoles). The resin is washed successively with DMF, $CH_2Cl_2$, $CH_3OH$, $CH_2Cl_2$. The reaction to ninhydrin is negative.

Liberation

The process is as described for cycle 32.

CYCLE 1

4 mMoles of S-p-methoxybenzyl ether of Boc-L-cysteine (1.13 g) is made to react in the conditions of cycle 31.

II—ELIMINATION OF THE DINITROPHENYL GROUP OF HISTIDINE 2 ml of mercaptoethanol is added to 15 ml of dimethylformamide (DMF), and the pH is adjusted to 8 with triethylamine. This reagent is introduced into the apparatus and the mixture is agitated for 14 hours. The resin is filtered and washed alternately with methylene chloride (3x), and with methanol (3x). After drying under vacuum, the weight of the resin is 2.85 g.

III LIBERATION OF THE PEPTIDE OF THE RESIN AND ELIMINATION OF THE PROTECTOR GROUPS 15 ml of hydrofluoric acid is distilled in a mixture of 1.5 g of resin-peptide and 1.5 ml of anisol. The mixture is agitated for 1 hr at 0° C. and for 30 min at ambient temperature. The acid is expelled under vacuum and the residue is taken up again in 3 times 5 ml of acetic acid and precipitated by ethyl ether free from peroxide. The precipitate is centrifuged cold, washed several times with ether, and dried under vacuum. The precipitate is taken up again by water and the insoluble residue is eliminated by centrifuging. The lyophilized solution provides 800 mg of product.

IV—PURIFICATION OF THE PEPTIDE

Two hundred milligrams of crude peptide are placed at the top of a column (diameter 2.5 cm, length 90 cm) of Biogel P6, (50–100 mesh), and are eluted with 0.1M acetic acid and fractions of 12 ml are collected by following the elution with a 280 nm recording device. The purified peptide is collected in the 23–28 fractions.

V—CYCLIZATION

The fractions containing the purified peptide are lyophilized and the residue is taken up again in 500 ml of 1M ammonium hydrogenocarbonate buffer, pH 8, and submitted to a bubbling of air through a porous plate for 24 hrs. The solution is lyophilized and the residue purified on a CMC 52 Whatman column by an ammonium acetate gradient of 0.6 mho to 7 mho, pH 4, with an LKB Ultrograd 11300 apparatus. After acid hydrolysis, the composition in amine acids is the following, referred to proline =2 (theoretical figures in brackets):

Ala (1) 1.05; Arg (1) 0.83; Asp (2) 2.10; Cys (2) 1.80; Glu (3) 3.10; Gly (3) 3.30; His (1) 0.80; Leu (5) 5.2; Lys (2) 1.90; Pro (2) 2.0; Ser (3) 3.10; Thr (4) 4.15; Tyr (1) 0.85; Val (2) 2.1.

EXAMPLE 2:

Obtaining the peptide with the following formula ($I_B$):

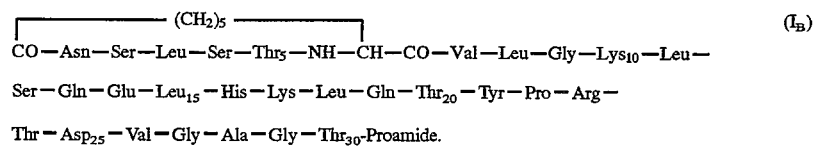

The t-Boc aminoacids carrying the lateral functions are obtained as indicated in example 1.

In the same way, the hydrolysis of the purified peptide is carried out in a sealed tube under vacuum in a 6N HCl medium (110° C., 24 hours).

SYNTHESIS OF THE 10–31 SEQUENCE OF THE PEPTIDE

1a) Preparation of the resin (P. Rivaille, A. Robinson, M. Kamen and G. Milhaud, Helv., 1971, 54, 2772).

Benzyl-ketoresin

In a 2 l. three-necked flask, fitted with an agitator, 50 g of polystyrene with 1% of divinylbenzene Bio-rad $SX_1$ (200–400 mesh) is left to swell in 350 ml of nitrobenzene. In another flask, 66 g of $AlCl_3$ is dissolved in 300 ml of nitrobenzene to which 80 ml of benzoyl chloride is added. The mixture is poured into the first flask under a good agitation which is maintained for two hours at ambient temperature. If the resin swells too much, nitrobenzene is added (about 100 ml). The mixture is filtered, washed with dioxan (3x), with acetic acid (3x), with methanol (3x) and finally, alternately, with $CH_2Cl_2$ and $CH_3OH$ in order to make the resin swell and contract each time leaving a sufficient contact time. The mixture is dried in a dessicator under vacuum all night (yield 75 g).

Benzylhydrylamine resin

In a 1 l. flask fitted with "Dean Stark" and an agitator, 500 g of ammonium formiate is heated to 120°–130° C., for 1 to 2 hours. The resin (50 g) is added in one go and the temperature is allowed to rise to 160°–165° C., over half an hour, under efficient agitation which is maintained for 6 hours. The mixture is filtered, washed with water, then treated as above for the benzylketoresin. The resin dried under vacuum is heated to reflux and agitated for 8 hours in 6N HCl. It is then filtered and washed as previously. The fixation capacity varies, according to the nature of the amino acid, between 0.3 and 0.5 mMole/g.

1b) Preparation of the 10–31 sequence of the peptide

The apparatus used allows a 25 ml pyrex tube, the central compartment of which contains the resin (2 g), to be agitated mechanically. At the ends of the tube, 2 fritted glass filters are intended for the introduction and then the elimination of the reagents (about 15 ml).

CYCLE 31

Coupling:

2 g of resin (fixation capacity 0.5 mMoles/g) is agitated (10 min) in a medium of $CH_2Cl_2$, $(CH_3)_2NCHO$ (DMF) (1:1, v/v) (10 ml) in the presence of Boc-L-proline (2 mM, 0.43 g). DCCI (4 mMoles) and 1-hydroxybenzotriazol (HOBT) (4 mMoles) are added and agitation is resumed for 2 hours. The resin is washed successively with $CH_2Cl_2$ (1x, 2 min), $CH_3OH$ abs (3x, 2 min), $CH_2Cl_2$ (3x, 2 min). The reaction with ninhydrin is carried out on a sample of resin: it is negative.

Liberation of the amino group:

The resin is treated by a $CF_3COOH$—$CH_2Cl_2$ mixture (1:1, v/v) for 1 min; the mixture is filtered and the operation is repeated leaving in contact for 15 min. The resin is washed with $CH_2Cl_2$ (3x, 1 min). $CF_3COOH$ is eliminated by treating the resin twice with an $ET_3N/CH_2Cl_2$ mixture (12.5:87.5 v/v) (contact time 1 min then 5 min). The mixture is washed with $CH_2Cl_2$ (8x, 1 min). The resin-L-proline is titrated: it contains 0.5 mMole/g of proline.

CYCLE 30

Coupling:

The resin-L-prolyl (1 mMoles) is agitated (10 min) with 4 mMoles of Boc-O-Benzyl-L-threonine (1.23 g) in $CH_2Cl_2$-DMF (1:1 v/v) (10 ml). DCCI (4 mMoles) and HOBT (4 mMoles) are added and agitation is resumed (2 hrs). The resin is washed successively: $CH_2Cl_2$ (1x, 2 min), $CH_3OH$ abs (3x, 2 min), $CH_2Cl_2$ (3x, 2 min). The reaction with ninhydrin is negative.

Liberation of the amino group—See cycle 31.

CYCLE 29 TO 24

The above coupling and liberation processes are used in making react for:

| Cycle 29 | 4 mMoles Boc-glycine (0.71 g) |
| Cycle 28 | 4 mMoles Boc-L-ala (0.76 g) |
| Cycle 27 | 4 mMoles Boc-glycine (0.71 g) |
| Cycle 26 | 4 mMoles Boc-L-valine (0.87 g) |
| Cycle 25 | 4 mMoles B-benzyl ester of Boc-L-aspartic acid (1.29 g) |
| Cycle 24 | 4 mMoles Boc-O-benzyl-L-threonine (1.24 g). |

CYCLE 23

Coupling:

The resin-peptide of cycle 24, previously washed with DMF (2x) is agitated (10 min) with 4 mMoles of Boc-N-γ-tosyl-L-arginine (1.41 g) in a solution of DMF and the following process is as described for cycle 30.

CYCLE 22

Coupling:

The resin-peptide of cycle 23 is agitated (10 min) with 4 mMoles of Boc-L-proline (0.88 g) in a medium of $CH_2Cl_2$ (10 ml). DCCI/HOBT is added as described for cycle 31. At the end of the reaction period, the reaction with ninhydrin was negative.

Liberation—See cycle 31.

CYCLES 21 TO 20

The coupling and liberation processes used in cycle 22 are used in making react:

| Cycle 21 | 4 mMoles Boc-O-Benzyl-L-tyrosine (1.49 g) |
| Cycle 20 | 4 mMoles Boc-O-Benzyl-L-threonine (1.24 g). |

CYCLE 19

Coupling:

The resin-peptide of cycle 20, previously washed with DMF (2x) is agitated (10 min) with 4 mMoles of Boc-L-glutamine p-nitrophenylester (1.5 g) and 10 ml of DMF with the addition of 1% acetic acid. DCCI (4 mMoles) and HOBT (4 mMoles) are added and the mixture is agitated for 48 hrs. The resin is washed with DMF, $CH_2Cl_2$, $CH_3OH$, $CH_2Cl_2$ (2x).

Liberation—See cycle 31.

CYCLES 18 TO 14

The process for cycle 30 is used in making react:

| Cycle 18 | 4 mMoles Boc-L-leucine (1.0 g) |
| Cycle 17 | 4 mMoles Boc-ε-carbobenzyloxy-L-lysine (1.52 g) |
| Cycle 16 | 4 mMoles Boc-dinitro-2,4-phenyl(im)L-histidine (1.23 g) |
| Cycle 15 | 4 mMoles Boc-L-leucine (1.0 g) |
| Cycle 14 | 4 mMoles γ-benzyl ester of Boc-L-glutamic acid (1.3 g). |

CYCLE 13

The process is as for cycle 19.

CYCLE 12

The process is as for cycle 30 using 4 mMoles of Boc-O-benzyl-L-serine (1.0 g).

CYCLES 11 and 10

The process is as for cycle 30 in making react:

| Cycle 11: | the derivative used in cycle 18. |
| Cycle 10: | the derivative used in cycle 17. |

2. SYNTHESIS OF THE 1–9 SEQUENCE OF THE PEPTIDE

2a) Partial sequence Boc-L-Thr (Bzl)-Asu OMe (A).

Z-Asu OMe (11.2 g) is introduced into MeOH—$H_2O$ (2:1, v/v) and the mixture is hydrogenated in the presence of palladiated carbon (14 hrs). The catalyst having been eliminated, the mixture is concentrated under vacuum. Dioxan (40 ml) is added, then triethylamine (4.2 ml) is added, while cooling, then Boc-L-Thr (Bzl) OSu (16 g) is added. After agitation (72 hrs), N,N-dimethylamino-1,3-propane diamine is introduced, and the mixture is agitated (4 hrs) then concentrated to one third. It is extracted with ethyl acetate (AcOEt), the AcOEt is washed with HCl (1N), then with $H_2O$; then distilled under vacuum. The oily residue is taken up in ether, extracted with $NaHCO_3$ (5%), re-extracted with AcOEt and washed successively with $H_2O$, HCl (1N), $H_2O$. The extracts are dried on anhydrous sodium sulphate, and the AcOEt is expelled. A is obtained in the form of an oily product (10 g).

2b) Partial sequence Boc-L-Ser (Bzl)-L-Thr (Bzl) Asu OMe.CHA (B).

Product A (5 g) is dissolved with cooling in TFA (15 ml). At ambient temperature, TFA is expelled under vacuum and the residue is dried under vacuum, then dissolved in DMF (10 ml) and the pH is brought to 6 by triethylamine (4 ml) while cooling. Then HOBT (5 g) and Boc-L-Ser (Bzl) OSu are added with agitation (3 days) at ambient temperature, and at pH 6. N,N-dimethylamino-1,3-propanediamine is added, with agitation, (1 hr), $H_2O$ is added, followed by extraction by AcOEt as described above. Cyclohexylamine (CHA) is added to the dried AcOEt, followed by distillation under reduced pressure. The oily product B is obtained (4 g).

2c) Partial sequence Boc-L-Asn-L-Ser(Bzl)-L-Leu-NH-$NH_2$ (C).

3 g of Boc-L-Asn-L-Ser-(Bzl)-L-Leu OEt is dissolved in 20 ml of $CH_3OH$, 10 ml of 80% $NH_2$—$NH_2$—$H_2O$ is added and the mixture is left for 14 hours at ambient temperature. It is then precipitated with ethyl ether, the precipitate is washed with ethyl ether and recrystallized from a mixture of $CH_3OH$-AcOEt-ethyl ether. 2.5 g of expected product is obtained (C).

2d) Partial sequence Boc-L-Asn-L-Ser (Bzl)-L-Leu-L-Ser (Bzl)-L-Thr (Bzl)-Asu OMe (D).

Product B (2 g) is introduced into AcOEt in the presence of HCl (1N); the mixture is dried on anhydrous sodium sulphate and concentrated under vacuum. TFA (6 ml) is added cold, with agitation at ambient temperature (0.5 hr), then the TFA is eliminated under vacuum and the residue is dried under vacuum. The residue is dissolved in DMF (2 ml), and after neutralization with triethylamine, is slowly introduced at –40° C. into a solution of C Boc-L-Asn-L-Ser(Bzl)-L-Leu-NH-$NH_2$ (1.7 g) in DMF (6 ml) to which dioxan (2.8 ml) has previously been added, in the presence of HCl (1N) and isoamyl nitrite (0.6 ml). The pH is adjusted to 7 with triethylamine, and reaction takes place at 5° C. (72 hrs).

The reactional mixture is slowly introduced at –5° C. into 0.5N HCl (60 ml). The precipitate is washed with $H_2O$. Extraction is done by $CHCl_3$ (100 ml), the extracts being washed successively with aqueous HCl (1N) NaCl. The $CHCl_3$ is eliminated. Product D is precipitated by a mixture of $CHCl_3$-n-hexane (2 g).

2e) Cyclization -L-Asn-L-Ser (Bzl)-L-Leu-L-Ser (Bzl)-L-Thr (Bzl) $Asu^{1,7}$—NH—$NH_2$ (E).

Product D (1.6 g) is dissolved in anhydrous pyridine (15 ml). TFA-ONP (2.5 g) is added, with agitation at 45° C. (3 hrs), followed by concentration under vacuum, precipitation by ethyl ether, treatment with TFA as above, then cyclization in anhydrous pyridine at 50° C. for 5 hours. Extraction is carried out by $CHCl_3$ and the extracts are washed as described above, then concentrated under vacuum, and precipitated by n-hexane.

The precipitate (2 g) is dissolved in DMF (5 ml) and $CH_3OH$ (25 ml). 15 ml of hydrazine (80%) is added, the mixture is agitated at ambient temperature (14 hrs) and $H_2O$ is added. The precipitate is filtered and washed with $H_2O$. $CH_3OH$ (50 ml) is added and the mixture is heated to reflux; the product E is precipitated (0.8 g).

2f) Preparation of the 1–9 sequence: -L-Asn-L-Ser (Bzl) -L-Leu-L-Ser (Bzl)-L-Thr (Bzl)-$Asu^{1,7}$-L-Val-L-Leu-Gly OH (F).

Product E (1 g) is put into suspension in DMF (4 ml), dioxan and N HCl (1.7 ml) are added at –5° C. Isoamyl nitrite (0.3 ml) is added at –10° C. under agitation. L-H-Val-L-Leu-Gly (0.9 g) is added at –5° C., the pH being brought to 7 by triethylamine. The mixture is agitated in an ice bath (48 hrs), then product F (1 g) is precipitated by 0.5N HCl, (150 ml).

3. PREPARATION OF PEPTIDE.

3a) HOBT (111 mg) and DCCI (150 mg) are added to product F (500 mg) dissolved in DMF (2 ml). Agitation is carried out for 72 hours in the presence of peptidyl resin 10–31 (300 mg) after elimination of t-Boc of $Lys_{10}$.

3b) Cleavage of the peptide according to Tam et al. JACS (1983), 105, 6442.

The quantities are referred to 1 g of peptidyl resin.

1) HF (2.5 ml) is distilled in a mixture of resin-peptide (1 g), dimethylsulphide (6.5 ml) and p-cresol (250 mg), with agitation (1 hr) at 0° C. The acid and the dimethylsulphide are expelled under vacuum and the residue is taken up 3 times by 5 ml of AcOEt.

2) The dried peptidyl resin suspended in dimethylsulphide (1 ml), is treated by liquid HF (10 ml) at 0° C. (1 hr). After elimination of the HF and the dimethylsulphide under vacuum, the resin is washed with ether (3 times 10 ml); the peptide is taken up with acetic acid, precipitated by ethyl ether, centrifuged cold, washed several times with ether, and dried under vacuum. The precipitate is taken up again by water and the insoluble residue is eliminated by centrifuging. The lyophilized solution produces 500 mg of product.

3c) Purification of the peptide.

200 mg of crude peptide is placed at the top of a column (diameter 2.5 cm, length 90 cm) of Biogel P6, 50–100 mesh. It is eluted by 0.1M acetic acid and fractions of 12 ml are collected by following the elution with a 280 nm recording device. The purified peptide is collected in the fractions 23–28. These fractions are lyophilized and the residue is purified on a Whatman CMC 32 column by ammonium acetate gradient of 0.6 mho to 7 mho, pH 4, with an LKB Ultrograd 11300 apparatus.

After acid hydrolysis, the composition in amino acids is the following, referred to proline=2 (theoretical figures in brackets):

Ala (1) 1.15; Arg (1) 0.85; Asp (2) 2.15; Glu (3) 3.10; Gly (3) 2.9; His (1) 0.83; Leu (5) 5.3; Lys (2) 1.95; Pro (2) 2.0; Ser (3) 3.20; Thr (4) 4.10; Tyr (1) 0.80; Val (2) 2.1; Asu (1) 0.93.

Abbreviations
AcOEt=ethyl acetate
Asu=α-aminosuberic acid
Bzl=Benzyl
CHA=Cyclohexylamine
DCHA=Dicyclohexylamine
ONP=p-nitrophenyl ester
OSu=N-hydroxysuccinimide ester
Z=Benzyloxycarbonyl

BIOLOGICAL ACTIVITY OF THE PRODUCTS OF THE EXAMPLES.

This is determined using male rats weighing from 100 to 120 g and having been without food for 16 hours. The activity is expressed in MRC units starting with the decrease in calcemia, measured one hour after intravenous injection of the peptide under test suitably diluted in a buffer of 0.1N sodium acetate pH 6 and 0.1% albumin, in comparison with the activity of the "Research Standard B" suitably diluted. The biological activity of the peptide of example 1 is higher than 4000 MRC units per mg and that of the peptide of example 2 is higher than 4500 MRC units per mg.

On account of this activity, the usual dose, which is variable according to the product used, the subject treated and the specific ailment, can be for example, from 1 to 100 MRC units per day by intramuscular or subcutaneous means.

I claim:

1. A polypeptide of formula (I):

$$X-A'_7-Leu-Gly-A'_{10}-A'_{11}-A'_{12}-Gln-A'_{14}-A'_{15}-A'_{16}-Lys-A'_{18}-A'_{19}-Thr-A'_{21}-Pro-A'_{23}-Thr-A'_{25}-A'_{26}-Gly-A'_{28}-Gly-A'_{30}-ProNH_2 \quad (I)$$

in which:

$A'_7$ is Val or Leu;
$A'_{10}$ is Lys or Thr;
$A'_{11}$ is Leu or Tyr;
$A'_{12}$ is Ser or Thr;
$A'_{14}$ is Glu or Asp;
$A'_{15}$ is Leu or Phe;
$A'_{16}$ is His or Asn;
$A'_{18}$ is Leu or Phe;
$A'_{19}$ is Gln or His;
$A'_{21}$ is Tyr or Phe;
$A'_{23}$ is Arg or Gln;
$A'_{25}$ is Asp, Asn or Ala;
$A'_{26}$ is Val, Thr or Ile;
$A'_{28}$ is Ala, Ser or Val;
$A'_{30}$ is Thr, Val or Ala;
and X is

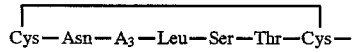

in which $A_3$ is Ser, Gly or Ala, or

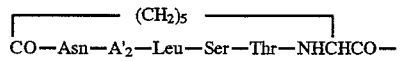

in which $A'_2$ is Ser, Gly or Ala.

2. A polypeptide of formula ($I_B$):

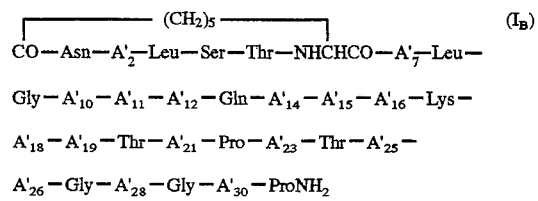

in which $A'_2$, $A'_7$, $A'_{10}$, $A'_{11}$, $A'_{12}$, $A'_{14}$, $A'_{15}$, $A'_{16}$, $A'_{18}$, $A'_{19}$, $A'_{21}$, $A'_{23}$, $A'_{25}$, $A'_{26}$, $A'_{28}$, and $A'_{30}$ are as defined in claim 1 and wherein the polypeptide contains α-amino-suberic acid (Asu) of which the ω-carboxyl is fixed to the amino group of Asn.

3. A polypeptide according to claim 2 in which $A'_7$ is a valine.

4. A polypeptide according to claim 2 which is:

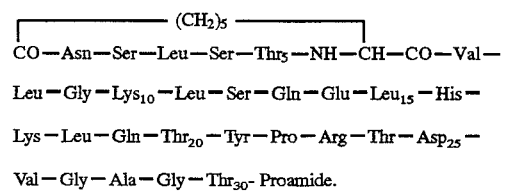

5. A pharmaceutical composition for lowering calcemia containing an effective mount for lowering calcemia of the polypeptide of claim 4 and a pharmaceutically acceptable carrier or excipient.

6. A process for the preparation of the polypeptide of claim 2 wherein the amino acids, the peptides or their combinations are submitted to condensation reactions in the order of the sequence of amino acids of formula ($I_B$), and wherein the solid phase technique for obtaining a 10–31 sequence and the classic liquid phase technique for obtaining a 1–9 sequence are combined.

7. A pharmaceutical composition for lowering calcemia containing an effective amount for lowering calcemia of the polypeptide of claim 2 and a pharmaceutically acceptable carrier or excipient.

8. A pharmaceutical composition according to claim 7 wherein $A'_7$ represents valine.

9. A pharmaceutical composition for lowering calcemia containing an effective mount for lowering calcemia of the polypeptide of claim 1 and a pharmaceutically acceptable carrier or excipient.

10. A polypeptide according to claim 1 which is:

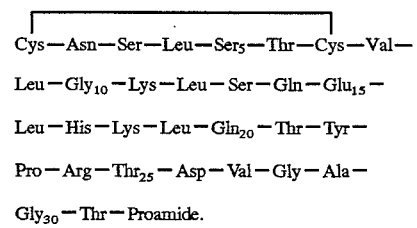

11. A pharmaceutical composition for lowering calcemia containing an effective mount for lowering calcemia of the polypeptide of claim 10 and a pharmaceutically acceptable carrier or excipient.

12. A polypeptide of formula ($I_A$):

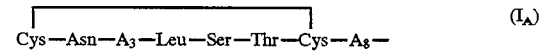

-continued $$\text{Leu}-\text{Gly}-A_{11}-A_{12}-A_{13}-\text{Gln}-A_{15}-$$
$$A_{16}-A_{17}-\text{Lys}-A_{19}-A_{20}-\text{Thr}-A_{22}-$$
$$\text{Pro}-A_{24}-\text{Thr}-A_{26}-A_{27}-\text{Gly}-A_{29}-$$
$$\text{Gly}-A_{31}-\text{ProNH}_2$$

in which:

$A_3$ is Ser, Gly or Ala;
$A_8$ is Val or Leu;
$A_{11}$ is Lys or Thr;
$A_{12}$ is Leu or Tyr;
$A_{13}$ is Ser or Thr;
$A_{15}$ is Glu or Asp;
$A_{16}$ is Leu or Phe;
$A_{17}$ is His or Asn;
$A_{19}$ is Leu or Phe;
$A_{20}$ is Gln or His;
$A_{22}$ is Tyr or Phe;
$A_{24}$ is Arg or Gln;
$A_{26}$ is Asp, Asn or Ala;
$A_{27}$ is Val, Thr or Ile;
$A_{29}$ is Ala, Ser or Val; and
$A_{31}$ is Thr, Val or Ala.

13. A polypeptide according to claim 12 in which $A_8$ is a valine.

14. A process for the preparation of the polypeptide of claim 12 wherein the amino acids, the peptides or their combinations are submitted to condensation reactions in the order of the sequence of amino acids of formula ($I_A$).

15. A pharmaceutical composition for lowering calcemia containing an effective mount for lowering calcemia of the polypeptide of claim 12 and a pharmaceutically acceptable carrier or excipient.

16. A pharmaceutical composition according to claim 15 wherein $A_8$ represents valine.

* * * * *